US012758625B2

(12) United States Patent
Poland et al.

(10) Patent No.: US 12,758,625 B2
(45) Date of Patent: Oct. 13, 2026

(54) ZIKA VIRUS POLYPEPTIDES

(71) Applicant: Mayo Foundation for Medical Education and Research, Rochester, MN (US)

(72) Inventors: Gregory A. Poland, Marco Island, FL (US); Inna G. Ovsyannikova, Rochester, MN (US); Richard B. Kennedy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 907 days.

(21) Appl. No.: 17/908,704

(22) PCT Filed: Mar. 1, 2021

(86) PCT No.: PCT/US2021/020217

§ 371 (c)(1),
(2) Date: Sep. 1, 2022

(87) PCT Pub. No.: WO2021/178281

PCT Pub. Date: Sep. 10, 2021

(65) Prior Publication Data

US 2024/0189412 A1 Jun. 13, 2024

Related U.S. Application Data

(60) Provisional application No. 62/984,520, filed on Mar. 3, 2020.

(51) Int. Cl.
*A61K 39/12* (2006.01)
*A61K 39/00* (2006.01)
*A61P 31/14* (2006.01)
*C07K 14/005* (2006.01)

(52) U.S. Cl.
CPC .............. *A61K 39/12* (2013.01); *A61P 31/14* (2018.01); *C07K 14/005* (2013.01); *A61K 2039/55505* (2013.01); *A61K 2039/55561* (2013.01); *A61K 2039/55566* (2013.01); *C12N 2770/24122* (2013.01); *C12N 2770/24134* (2013.01)

(58) Field of Classification Search
CPC ............................................ C12N 2770/24134
See application file for complete search history.

(56) References Cited

U.S. PATENT DOCUMENTS

| | | | | |
|---|---|---|---|---|
| 2015/0374811 | A1 | 12/2015 | Malley et al. | |
| 2017/0296646 | A1* | 10/2017 | Hernandez .............. | A61P 31/14 |
| 2019/0023745 | A1 | 1/2019 | Baric et al. | |
| 2019/0134184 | A1 | 5/2019 | Yu et al. | |
| 2019/0255125 | A1* | 8/2019 | Despres ................ | A61K 39/12 |

FOREIGN PATENT DOCUMENTS

| | | | |
|---|---|---|---|
| KR | 10-2018-0127397 | A | 11/2018 |
| WO | 2008/043774 | A1 | 4/2008 |
| WO | 2013/003579 | A1 | 1/2013 |
| WO | 2015/130488 | A2 | 9/2015 |
| WO | 2015/175361 | A1 | 11/2015 |
| WO | 2017/109223 | A1 | 6/2017 |
| WO | 2017/140905 | A1 | 8/2017 |
| WO | 2017/156511 | A1 | 9/2017 |
| WO | 2018/127689 | A1 | 7/2018 |
| WO | 2018/148499 | A1 | 8/2018 |
| WO | 2018/218355 | A1 | 12/2018 |
| WO | 2018/237313 | A1 | 12/2018 |
| WO | 2019/058133 | A2 | 3/2019 |
| WO | 2019/135086 | A1 | 7/2019 |
| WO | 2019/186199 | A1 | 10/2019 |
| WO | 2019/186200 | A1 | 10/2019 |
| WO | 2019/220150 | A1 | 11/2019 |
| WO | 2021/245140 | A2 | 12/2021 |
| WO | 2022/175330 | A1 | 8/2022 |
| WO | 2022/253917 | A1 | 12/2022 |

OTHER PUBLICATIONS

Crooke, Stephen N., et al. "Identification of naturally processed Zika virus peptides by mass spectrometry and validation of memory T cell recall responses in Zika convalescent subjects." PLoS One 16.6 (2021): e0252198. (Year: 2021).*

Belyakov et al., "Mucosal immunization with HIV-1 peptide vaccine induces mucosal and systemic cytotoxic T lymphocytes and protective immunity in mice against intrarectal recombinant HIV-vaccinia challenge," *PNAS*, 95:1709-1714 (1998).

Bounds et al., "An immunoinformatics-derived DNA vaccine encoding human class II T cell epitopes of Ebola virus, Sudan virus, and Venezuelan equine encephalitis virus is immunogenic in HLA transgenic mice," *Hum. Vaccin. Immunother.*, 13(12):2824-2836 (2017).

Gatherer et al., "Zika virus: a previously slow pandemic spreads rapidly through the Americas," *J. Gen. Virol.*, 97(2):269-273 (2016).

Hekele et al., "Rapidly produced SAM® vaccine against H7N9 influenza is immunogenic in mice," *Emerg. Microbes Infect.*, 2(8):e52, 7 pages (2013).

International Search Report issued in PCT/US2021/020217, mailed on Aug. 5, 2021.

Jackson et al., "A totally synthetic vaccine of generic structure that targets Toll-like receptor 2 on dendritic cells and promotes antibody or cytotoxic T cell responses," *PNAS*, 101:15440-15445 (2004).

Krauer et al., "Zika Virus Infection as a Cause of Congenital Brain Abnormalities and Guillain-Barré Syndrome: Systematic Review," *PLOS Med.*, 14(1):e1002203 (2017).

(Continued)

*Primary Examiner* — Robert J Yamasaki
(74) *Attorney, Agent, or Firm* — Arnold & Porter Kaye Scholer LLP

(57) ABSTRACT

This document provides methods and materials related to selected Zika virus polypeptides. For example. vaccine compositions that contain one or more selected Zika virus polypeptides provided herein and that have the ability to increase immune responses against flaviviruses such as Zika viruses within a mammal (e.g., a human) are provided.

22 Claims, 1 Drawing Sheet

Specification includes a Sequence Listing.

(56) References Cited

OTHER PUBLICATIONS

Makarkov et al., "Plant-derived virus-like particle vaccines drive cross-presentation of influenza A hemagglutinin peptides by human monocyte-derived macrophages," *NPJ Vaccines*, 15(4): 17, 12 pages (2019).
Mirza et al., "Towards peptide vaccines against Zika virus: Immunoinformatics combined with molecular dynamics simulations to predict antigenic epitopes of Zika viral proteins," *Sci. Rep.*, 6:37313, 17 pages (2016).
Parlane et al., "Heterologous peptide display on chromatin nanofibers: A new strategy for peptide vaccines," *Biochem. Biophys. Res. Commun.*, 524:825-831 (2020).
Prasasty et al., "Peptide-Based Subunit Vaccine Design of T- and B-Cells Multi-Epitopes against Zika Virus Using Immunoinformatics Approaches," *Microorganisms*, 7(8):226, 27 pages (2019).
Stawikowski et al., "Introduction to Peptide Synthesis," *Current Protocols in Protein Science*, 26(1):18.1.1-18.1.9 (2001).
Supplementary European Search Report dated Feb. 22, 2024, from European Application EP 21765466, 3 pages.
Didierlaurent et al., "AS04, an aluminum salt- and TLR4 agonist-based adjuvant system, induces a transient localized innate immune response leading to enhanced adaptive immunity," *J Immunol.*, 183(10):6186-6197 (Nov. 2009) Abstract only.
Seubert et al., "Adjuvanticity of the oil-in-water emulsion MF59 is independent of Nlrp3 inflammasome but requires the adaptor protein MyD88," *PNAS*, 108(27):11169-11174 (Jul. 2011).
Dikhit et al., "Computational prediction and analysis of potential antigenic CTL epitopes in Zika virus: A first step towards vaccine development," *Infection, Genetics and Evolution*, 45:187-197 (Nov. 2016).

* cited by examiner

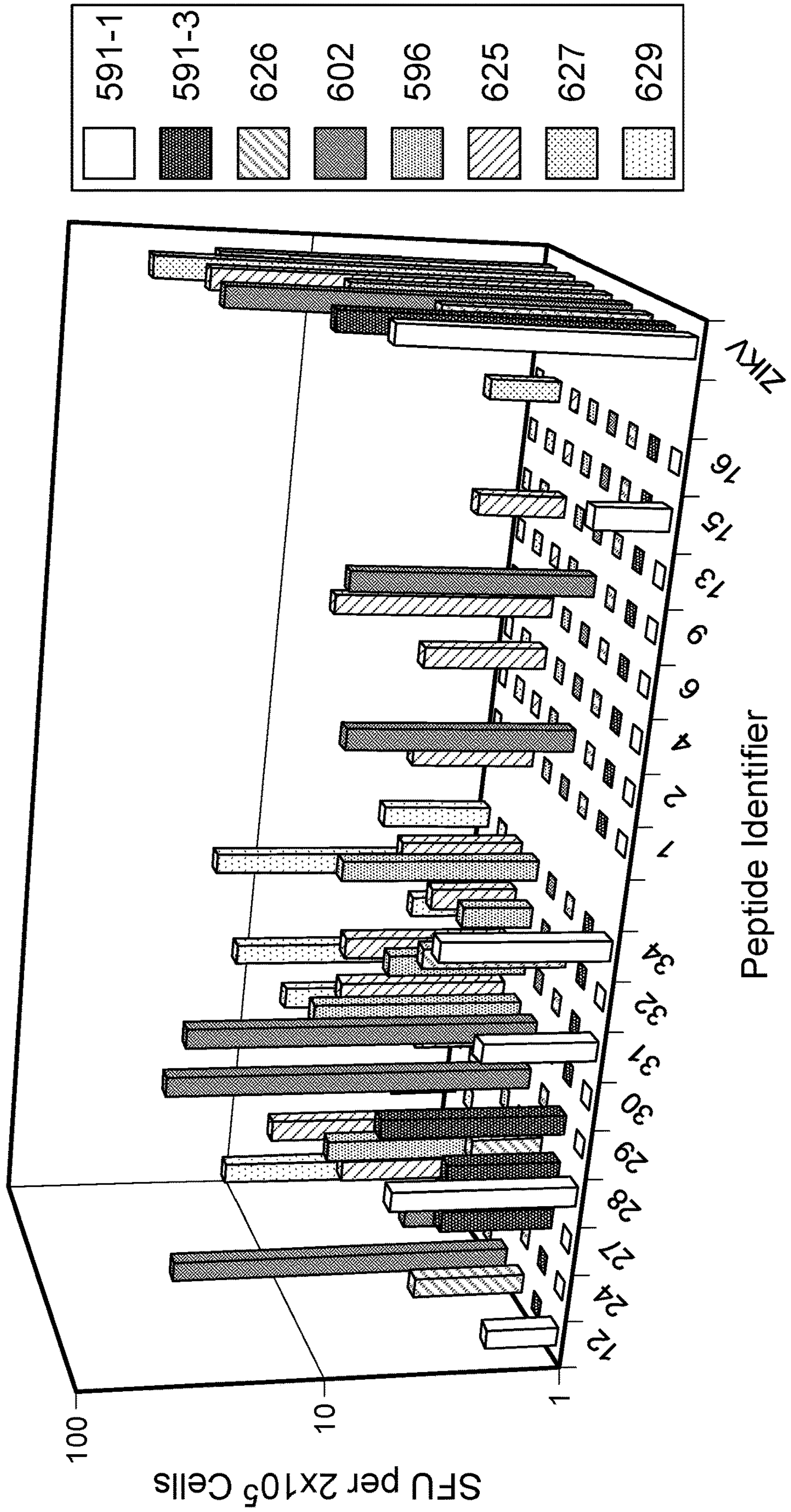
591-1
591-3
626
602
596
625
627
629
SFU per 2x10⁵ Cells
100
10
1
Peptide Identifier
12
24
27
28
29
30
31
32
34
1
2
4
6
9
13
15
16
ZIKV

ZIKA VIRUS POLYPEPTIDES

CROSS-REFERENCE TO RELATED APPLICATIONS

This application is a U.S. National Stage under 35 U.S.C. § 371 of International Application No. PCT/US2021/020217 filed Mar. 1, 2021 (published as WO 2021/178281 on Sep. 10, 2021), which claims the benefit of U.S. Provisional Application Ser. No. 62/984,520, filed Mar. 3, 2020. The disclosure of each of which is incorporated herein by reference in their entireties.

INCORPORATION OF SEQUENCE LISTING

The instant application contains a Sequence Listing which has been submitted electronically in ASCII format and is hereby incorporated by reference in its entirety. Said ASCII copy, created on Aug. 31, 2022, is named Seq_Listing-P35124US01.txt, and is 13,702 bytes in size.

TECHNICAL FIELD

This document provides methods and materials related to selected Zika virus polypeptides. For example, this document provides vaccine compositions that contain one or more selected Zika virus polypeptides provided herein and that have the ability to increase immune responses against flaviviruses such as Zika viruses within a mammal (e.g., a human).

BACKGROUND INFORMATION

Once an obscure pathogen, Zika virus (ZIKV) has emerged as a global public health problem. Since 2007, ZIKV has spread across the Pacific and South America, resulting in highly publicized outbreaks during 2015-2016 (Gatherer et al., J. Gen. Virol. 97:269-273 (2016)). Local ZIKV transmission has also been reported in the continental United States, and about 60% of the U.S. population resides in areas permissible to seasonal transmission by Aedes spp. mosquito vectors. Strong evidence has linked ZIKV infection in pregnant women with a number of fetal malformations and neurological abnormalities, emphasizing the need for an effective vaccine to combat the spread of this emerging disease (Krauer et al., PLOS Med. 14:e1002203 (2017)).

SUMMARY

This document provides methods and materials related to selected Zika virus polypeptides. For example, this document provides the isolated polypeptides set forth in Table 1, Table 2, and Table 3. In some cases, a selected Zika virus polypeptide provided herein can be a substantially pure polypeptide that comprises, consists essentially of, or consists of the amino acid sequence set forth in any one of SEQ ID NOs:1-17. This document also provides vaccine compositions that contain one or more selected Zika virus polypeptides provided herein and that have the ability to increase immune responses against flaviviruses such as Zika viruses within a mammal (e.g., a human), methods and materials for making vaccine compositions that contain one or more selected Zika virus polypeptides provided herein and that have the ability to increase immune responses against flaviviruses such as Zika viruses within a mammal (e.g., a human), kits containing one or more selected Zika virus polypeptides provided herein, methods for using such kits to identify mammals (e.g., humans) as having had a past or as having a current Zika virus infection, and methods for using such kits to identify a mammal (e.g., a human) as having humoral immunity specifically against a flavivirus such as a Zika virus.

As described herein, selected Zika virus polypeptides were identified as having the ability to induce broad recall immune responses against Zika viruses.

In general, one aspect of this document features a substantially pure polypeptide consisting essentially of or consisting of the amino acid sequence set forth in any one of SEQ ID NOs:1-17. The polypeptide can be covalently conjugated to a stabilizer selected from the group consisting of sucrose, lactose, a monosodium salt of glutamic acid, human serum albumin, and gelatin.

In another aspect, this document features a composition comprising at least four polypeptides, wherein each of the at least four polypeptides is a polypeptide consisting essentially of or consisting of the amino acid sequence set forth in any one of SEQ ID NOs: 1-17. Each of the at least four polypeptides can be a polypeptide consisting of the amino acid sequence set forth in any one of SEQ ID NOs:1-17. Each of the at least four polypeptides can be a polypeptide consisting of the amino acid sequence set forth in any one of SEQ ID NOs:1-9. The composition can comprise a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:3, a polypeptide consisting of the amino acid sequence set forth in SEQ ID NO:4, a polypeptide consisting of the amino acid sequence set forth in SEQ ID NO:5, a polypeptide consisting of the amino acid sequence set forth in SEQ ID NO:6, a polypeptide consisting of the amino acid sequence set forth in SEQ ID NO:7, a polypeptide consisting of the amino acid sequence set forth in SEQ ID NO:7, and a polypeptide consisting of the amino acid sequence set forth in SEQ ID NO:9. The composition can comprise an adjuvant. The adjuvant can be selected from the group consisting of a CpG oligonucleotide motif, aluminum sulfate, aluminum hydroxide, aluminum phosphate, aluminum potassium sulfate, monophosphoryl lipid A, aluminumphosphylate, MF59, AS03, and AS04.

In another aspect, this document features a method for increasing an immune response against a flavivirus in a mammal. The method comprises, consists essentially of, or consists of administering to the mammal a composition comprising a polypeptide consisting essentially of or consisting of the amino acid sequence set forth in any one of SEQ ID NOs:1-17. The mammal can be a human. The flavivirus can be a Zika virus. The composition can comprise an adjuvant. The adjuvant can be selected from the group consisting of a CpG oligonucleotide motif, aluminum sulfate, aluminum hydroxide, aluminum phosphate, aluminum potassium sulfate, monophosphoryl lipid A, aluminumphosphylate, MF59, AS03, and AS04. The composition can comprise at least four polypeptides, wherein each of the at least four polypeptides is a polypeptide consisting essentially of or consisting of the amino acid sequence set forth in any one of SEQ ID NOs:1-17. Each of the at least four polypeptides can be a polypeptide consisting of the amino acid sequence set forth in any one of SEQ ID NOs:1-17. Each of the at least four polypeptides can be a polypeptide consisting of the amino acid sequence set forth in any one of SEQ ID NOs: 1-9. The composition can comprise a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:3, a polypeptide consisting of the amino acid sequence set forth in SEQ ID NO:4, a polypeptide consisting of the amino acid sequence set forth in SEQ ID NO:5, a polypeptide consisting of the amino acid sequence set forth in SEQ ID NO:6, a polypeptide consisting of the amino acid sequence set forth in SEQ ID NO:7, a polypeptide consisting of the amino acid sequence set forth in SEQ ID NO:7, and a polypeptide consisting of the amino acid sequence set forth in SEQ ID NO:9.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below: All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1. IFN-γ ELISpot analysis focused on responses for candidate polypeptides (left cluster) and comparator polypeptides (right cluster). ZIKV responses for all subjects shown for comparison. SFU refers to Spot Forming Units and represents the number of T cells that recognize each peptide by secreting IFN-γ.

DETAILED DESCRIPTION

This document provides methods and materials related to selected Zika virus polypeptides. For example, this document provides the isolated polypeptides set forth in Table 1, Table 2, and Table 3. In some cases, a selected Zika virus polypeptide provided herein can be a substantially pure polypeptide that comprises, consists essentially of, or consists of the amino acid sequence set forth in any one of SEQ ID NOs:1-17. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel. In some cases, a substantially pure polypeptide provided herein can be a polypeptide that is synthesized to have a purity of at least about 60, 65, 70, 75, 80, 85, 90, 95, or 99 percent.

TABLE 1

Exemplary Zika virus polypeptides.

| Polypeptide Sequence | SEQ ID NO: | Peptide Identifier for FIG. 1 |
|---|---|---|
| YLQDGLIASL | 1 | 12 |
| TVVVGSVKNPMWRGPQRLPVPVN | 2 | 24 |
| FLRFTAIKPSLG | 3 | 27 |
| QVASAGITY | 4 | 28 |
| SLINGVVRL | 5 | 29 |
| GGLKRLPAGLLLGHGPI | 6 | 30 |
| VVDGDTLK | 7 | 31 |
| DGIEESDLIIPKSLAGP | 8 | 32 |
| RIIGDEEKY | 9 | 34 |

TABLE 2

Exemplary Zika virus polypeptides used as comparator polypeptides in FIG. 1.

| Polypeptide Sequence | SEQ ID NO: | Peptide Identifier for FIG. 1 |
|---|---|---|
| GRGPQRLPVP | 10 | 1 |
| ALALAIIKY | 11 | 2 |
| RQDQRGSGQVVTY | 12 | 4 |
| TVTRNAGLVKRR | 13 | 6 |
| YLIPGLQAA | 14 | 9 |
| LTVVVGSVKNPMGRGPQRLPVPVN | 15 | 13 |
| IIPKSLAGPLSHHNTREGYRTQ | 16 | 15 |
| RGPQRLPVPVN | 17 | 16 |

In some cases, a Zika virus polypeptide provided herein that consists essentially of the amino acid sequence set forth in any one of SEQ ID NOs:1-17 is a polypeptide that has zero, one, or two amino acid substitutions within the articulated sequence of the sequence identifier (e.g., SEQ ID NO:1), has zero, one, two, three, four, or five amino acid residues preceding the articulated sequence of the sequence identifier (e.g., SEQ ID NO:1), and/or has zero, one, two, three, four, or five amino acid residues following the articulated sequence of the sequence identifier (e.g., SEQ ID NO:1), provided that the Zika virus polypeptide has the ability to increase immune responses against a flavivirus such as a Zika virus within a mammal (e.g., a human). Examples of Zika virus polypeptides that consist essentially of the amino acid sequence set forth in any one of SEQ ID NOs:1-17 are set forth in Table 3.

TABLE 3

Exemplary Zika virus polypeptides.

| Polypeptide Sequence | SEQ ID NO: |
|---|---|
| LLDNIYLQDGLIASLYRPEA | 18 |
| LDNIYLQDGLIASLYRPE | 19 |
| DNIYLQDGLIASLYRP | 20 |
| NIYLQDGLIASLYR | 21 |
| IYLQDGLIASLY | 22 |
| NGVQLTVVVGSVKNPMGRGPQRLPVPVNELPHG GVQLTVVVGSVKNPMGRGPQRLPVPVNELPH | 23 |
| VQLTVVVGSVKNPMGRGPQRLPVPVNELP | 24 |
| QLTVVVGSVKNPMGRGPQRLPVPVNEL | 25 |
| LTVVVGSVKNPMGRGPQRLPVPVNE | 26 |
| LAILAFLRFTAIKPSLGLINRW | 27 |
| AILAFLRFTAIKPSLGLINR | 28 |
| ILAFLRFTAIKPSLGLIN | 29 |
| LAFLRFTAIKPSLGLI | 30 |
| AFLRFTAIKPSLGL | 31 |
| VWLAYQVASAGITYTDRRW | 32 |
| WLAYQVASAGITYTDRR | 33 |
| LAYQVASAGITYTDR | 34 |
| AYQVASAGITYTD | 35 |
| YQVASAGITYT | 36 |
| QGSASSLINGVVRLLSKPW | 37 |
| GSASSLINGVVRLLSKP | 38 |
| SASSLINGVVRLLSK | 39 |
| ASSLINGVVRLLS | 40 |
| SSLINGVVRLL | 41 |
| RVSPFGGLKRLPAGLLLGHGPIRMVLA | 42 |
| VSPFGGLKRLPAGLLLGHGPIRMVL | 43 |
| SPFGGLKRLPAGLLLGHGPIRMV | 44 |
| PFGGLKRLPAGLLLGHGPIRM | 45 |
| FGGLKRLPAGLLLGHGPIR | 46 |
| TNNSFVVDGDTLKECPLK | 47 |
| NNSFVVDGDTLKECPL | 48 |
| NSFVVDGDTLKECP | 49 |
| SFVVDGDTLKEC | 50 |
| FVVDGDTLKE | 51 |
| HTLWTDGIEESDLIIPKSLAGPLSHHN | 52 |
| TLWTDGIEESDLIIPKSLAGPLSHH | 53 |
| LWTDGIEESDLIIPKSLAGPLSH | 54 |
| WTDGIEESDLIIPKSLAGPLS | 55 |

TABLE 3-continued

Exemplary Zika virus polypeptides.

| Polypeptide Sequence | SEQ ID NO: |
|---|---|
| TDGIEESDLIIPKSLAGPL | 56 |
| VNMVRRIIGDEEKYMDYLS | 57 |
| NMVRRIIGDEEKYMDYL | 58 |
| MVRRIIGDEEKYMDY | 59 |
| VRRIIGDEEKYMD | 60 |
| RRIIGDEEKYM | 61 |

A polypeptide provided herein (e.g., a substantially pure polypeptide that comprises, consists essentially of, or consists of the amino acid sequence set forth in any one of SEQ ID NOs:1-17) can be any appropriate length. For example, a polypeptide provided herein (e.g., a substantially pure polypeptide that comprises, consists essentially of, or consists of the amino acid sequence set forth in any one of SEQ ID NOs:1-17) can be from nine amino acid residues to 100 amino acid residues (e.g., from nine amino acid residues to 90 amino acid residues, from nine amino acid residues to 80 amino acid residues, from nine amino acid residues to 70 amino acid residues, from nine amino acid residues to 60 amino acid residues, from nine amino acid residues to 50 amino acid residues, from nine amino acid residues to 40 amino acid residues, from nine amino acid residues to 35 amino acid residues, from nine amino acid residues to 30 amino acid residues, from nine amino acid residues to 25 amino acid residues, from nine amino acid residues to 24 amino acid residues, from nine amino acid residues to 23 amino acid residues, from nine amino acid residues to 22 amino acid residues, from nine amino acid residues to 21 amino acid residues, from nine amino acid residues to 20 amino acid residues, from nine amino acid residues to 19 amino acid residues, from nine amino acid residues to 18 amino acid residues, from nine amino acid residues to 17 amino acid residues, from nine amino acid residues to 16 amino acid residues, from nine amino acid residues to 15 amino acid residues, from 10 amino acid residues to 100 amino acid residues, from 11 amino acid residues to 100 amino acid residues, from 12 amino acid residues to 100 amino acid residues, from 13 amino acid residues to 100 amino acid residues, from 14 amino acid residues to 100 amino acid residues, from 15 amino acid residues to 100 amino acid residues, from 16 amino acid residues to 100 amino acid residues, from 17 amino acid residues to 100 amino acid residues, from 18 amino acid residues to 100 amino acid residues, from 19 amino acid residues to 100 amino acid residues, from 20 amino acid residues to 100 amino acid residues, from 21 amino acid residues to 100 amino acid residues, from 22 amino acid residues to 100 amino acid residues, from 23 amino acid residues to 100 amino acid residues, from 24 amino acid residues to 100 amino acid residues, from 25 amino acid residues to 100 amino acid residues, from 10 amino acid residues to 80 amino acid residues, from 10 amino acid residues to 50 amino acid residues, from 10 amino acid residues to 30 amino acid residues, from 10 amino acid residues to 25 amino acid residues, or from 10 amino acid residues to 20 amino acid residues) in length.

A polypeptide provided herein (e.g., a substantially pure polypeptide that comprises, consists essentially of, or consists of the amino acid sequence set forth in any one of SEQ ID NOs:1-17) can have the ability to increase an immune response against a flavivirus such as a Zika virus within a mammal (e.g., a human). For example, after administering a polypeptide provided herein (e.g., a substantially pure polypeptide that comprises, consists essentially of, or consists of the amino acid sequence set forth in any one of SEQ ID NOs:1-17) or nucleic acid encoding a polypeptide provided herein (e.g., nucleic acid encoding a polypeptide that comprises, consists essentially of, or consists of the amino acid sequence set forth in any one of SEQ ID NOs:1-17) to a mammal (e.g., a human), that mammal can generate an increased immune response (e.g., an increased antibody response and/or an increased T cell response) against a flavivirus such as a Zika virus. Any appropriate method can be used to identify the development of an increased immune response against a flavivirus such as a Zika virus. For example, a kit provided herein that includes one or more polypeptides provided herein can be used to assess a sample obtained from a mammal being tested for the presence, absence, or level of antibodies having the ability to bind to those polypeptides.

Any appropriate method can be used to obtain a polypeptide provided herein (e.g., a substantially pure polypeptide that comprises, consists essentially of, or consists of the amino acid sequence set forth in any one of SEQ ID NOs:1-17). For example, a polypeptide provided herein (e.g., a substantially pure polypeptide that comprises, consists essentially of, or consists of the amino acid sequence set forth in any one of SEQ ID NOs:1-17) can be obtained by isolating the polypeptide of interest from cells expressing the polypeptide (e.g., cells engineered to express the polypeptide of interest from exogenous nucleic acid encoding that polypeptide or cells infected with a virus (e.g., a Zika virus) that express the polypeptide of interest from that virus) or by synthesizing the polypeptide of interest using appropriate solid-phase peptide synthesis techniques such as those described elsewhere (Introduction to Peptide Synthesis. Gregg B. Fields. Current Protocols in Protein Science. Vol 26, Issue 1: Pages 18.1.1-18.1.9 (2001)).

This document also provides nucleic acid encoding a polypeptide provided herein (e.g., a polypeptide that comprises, consists essentially of, or consists of the amino acid sequence set forth in any one of SEQ ID NOs:1-17). For example, this document provides plasmids and viral vectors that include nucleic acid encoding a polypeptide provided herein (e.g., a polypeptide that comprises, consists essentially of, or consists of the amino acid sequence set forth in any one of SEQ ID NOs:1-17) in a manner such that the polypeptide can be expressed within a cell. In some cases, nucleic acid encoding a polypeptide provided herein (e.g., a polypeptide that comprises, consists essentially of, or consists of the amino acid sequence set forth in any one of SEQ ID NOs:1-17) can include a regulatory nucleic acid sequence (e.g., a promoter sequence) that is operably linked to the polypeptide-encoding sequence such that the polypeptide is expressed within a cell. Examples of promoter sequences that can be used as described herein include, without limitation, CMV promoters, EF1a promoters, SV40 promoters, PGK1 promoters, Ubc promoters, CAG promoters, Tetracycline response element promoters, and H1 promoters.

This document also provides compositions that include one or more (e.g., one, two, three, four, five, six, seven, eight, nine, ten, 11, 12, 13, 14, 15, 16, 17, 18, 19, 20, or more) of the polypeptides provided herein and/or nucleic acid encoding one or more (e.g., one, two, three, four, five, six, seven, eight, nine, ten, 11, 12, 13, 14, 15, 16, 17, 18, 19, 20, or more) of the polypeptides provided herein. For example, a composition provided herein can include at least four (e.g., four, five, six, seven, or eight) of the polypeptides set forth in Table 1 (or nucleic acid encoding those polypeptides). In some cases, a composition provided herein can include each of the polypeptides set forth in Table 1 (or nucleic acid encoding those polypeptides). In some cases, a composition provided herein can include at least four (e.g., four, five, six, or seven) of the polypeptides set forth in Table 2 (or nucleic acid encoding those polypeptides). In some cases, a composition provided herein can include each of the polypeptides set forth in Table 2 (or nucleic acid encoding those polypeptides). Examples of other specific combinations of polypeptides that can be used to make a composition provided herein include, without limitation, those set forth in Table 4.

TABLE 4

Exemplary combinations of polypeptides (or nucleic acid encoding those polypeptides).

| Composition Number | Combination of polypeptides (or nucleic acid encoding those polypeptides) |
|---|---|
| 1 | SEQ ID NO: 1 + SEQ ID NO: 2 + SEQ ID NO: 4 + SEQ ID NO: 5 + SEQ ID NO: 7 + SEQ ID NO: 8 + SEQ ID NO: 9 |
| 2 | SEQ ID NO: 3 + SEQ ID NO: 4 + SEQ ID NO: 5 + SEQ ID NO: 7 |
| 3 | SEQ ID NO: 1 + SEQ ID NO: 2 + SEQ ID NO: 3 + SEQ ID NO: 4 + SEQ ID NO: 5 + SEQ ID NO: 6 + SEQ ID NO: 7 + SEQ ID NO: 8 + SEQ ID NO: 9 |
| 4 | SEQ ID NO: 1 + SEQ ID NO: 3 + SEQ ID NO: 5 + SEQ ID NO: 7 + SEQ ID NO: 9 |
| 5 | SEQ ID NO: 3 + SEQ ID NO: 6 |
| 6 | SEQ ID NO: 2 + SEQ ID NO: 4 + SEQ ID NO: 6 + SEQ ID NO: 8 |
| 7 | SEQ ID NO: 1 + SEQ ID NO: 2 + SEQ ID NO: 3 + SEQ ID NO: 5 |
| 8 | SEQ ID NO: 1 + SEQ ID NO: 2 + SEQ ID NO: 6 + SEQ ID NO: 5 |
| 9 | SEQ ID NO: 1 + SEQ ID NO: 6 + SEQ ID NO: 7 + SEQ ID NO: 9 |
| 10 | SEQ ID NO: 4 + SEQ ID NO: 6 + SEQ ID NO: 7 + SEQ ID NO: 8 |

Any appropriate method can be used to formulate a composition provided herein (e.g., a composition that includes one, two, three, four, five, six, seven, eight, nine, ten, 11, 12, 13, 14, 15, 16, 17, 18, 19, 20, or more of the polypeptides provided herein and/or nucleic acid encoding one, two, three, four, five, six, seven, eight, nine, ten, 11, 12, 13, 14, 15, 16, 17, 18, 19, 20, or more of the polypeptides provided). For example, the one or more polypeptides provided herein (and/or nucleic acid encoding such one or more polypeptides) can be combined with a pharmaceutically acceptable carrier and/or a pharmaceutical excipient. The term "pharmaceutically acceptable" refers to generally non-toxic, inert, and/or physiologically compatible compounds. A term "pharmaceutical excipient" includes materials such as carriers, pH-adjusting and buffering agents, tonicity adjusting agents, wetting agents, colorants, and preservatives.

In some cases, a composition provided herein (e.g., a composition that includes one or more of the polypeptides provided herein and/or nucleic acid encoding one or more of the polypeptides provided herein) can be a vaccine composition. For example, a composition containing four or more polypeptides set forth in SEQ ID NOs:1-9 can be formulated into a polypeptide-based vaccine for use in a mammal (e.g., a human). Any appropriate method can be used to formulate a polypeptide-based vaccine such as those described elsewhere (Belyakov et al., *Proc. Natl. Acad. Sci.* U.S.A., 95:1709-1714 (1998); Jackson et al., *Proc. Natl. Acad. Sci.* U.S.A., 101:15440-15445 (2004); Makarkov et al., *NPJ Vaccines,* 15(4):17 (2019)); Hekele et al., *Emerg. Microbes Infect.,* 2(8):e52 (2013); Parlane et al, *Biochem. Biophys. Res. Commun.*, pii:S0006-291X(20)30264-3 (2020); and Bounds et al., *Hum. Vaccin. Immunother.,* 13(12):2824-2836 (2017)). In some cases, a vaccine composition provided herein can include one or more polypeptides provided herein (e.g., four or more different polypeptides that comprise, consist essentially of, or consist of the amino acid sequence set forth in any of SEQ ID NOs:1-17) in combination with one or more adjuvants. Examples of adjuvants that can be included within a vaccine composition provided herein include, without limitation, CpG oligonucleotide motifs, aluminum (e.g., aluminum salts, such as aluminum sulfate, aluminum hydroxide, aluminum phosphate, and aluminum potassium sulfate), monophosphoryl lipid A, aluminum hydroxyphosphate sulfate, MF59, AS03, AS04, CpG1018, and $ASO1_B$. In some cases, an adjuvant included within a vaccine composition provided herein can be a non-naturally occurring (e.g., artificial) adjuvant. In some cases, a vaccine composition provided herein can include one or more polypeptides provided herein (e.g., four or more different polypeptides that comprise, consist essentially of, or consist of the amino acid sequence set forth in any of SEQ ID NOs:1-17), one or more adjuvants, and one or more pharmaceutically acceptable carriers and/or pharmaceutical excipients.

In some cases, a polypeptide of a vaccine composition provided herein can be conjugated to, for example, a polysaccharide (e.g., sucrose or lactose), an amino acid (e.g., glycine or the monosodium salt of glutamic acid), and/or a protein (e.g., human serum albumin or gelatin) to improve stability or immunogenicity of the vaccine composition. In some cases, a polypeptide provided herein can be formulated into a vaccine composition in combination with a delivery vehicle such as a nanoparticle. For example, four or more polypeptides provided herein can be included within (e.g., embedded or displayed on the surface of) a nanoparticle.

In some cases, a vaccine composition provided herein can be a multivalent vaccine composition having the ability to increase immune responses against multiple members of the flavivirus family within a mammal (e.g., a human). For example, a vaccine composition provided herein can have the ability to increase immune responses against a Zika virus, a Dengue virus, a West Nile virus, a yellow fever virus, or any combination thereof. In some cases, a vaccine composition provided herein can be used as a multivalent vaccine composition having the ability to increase immune responses against one or more lineages, clades, or strains of Zika virus. For example, a vaccine composition provided herein can have the ability to increase immune responses against an East African Zika virus, a West African Zika virus, an Asian Zika virus, a South American Zika virus, or any combination thereof.

This document also provides methods for increasing an immune response against a flavivirus such as a Zika virus within a mammal (e.g., a human). For example, a vaccine composition provided herein can be administered to a mammal (e.g., a human) to increase an immune response (e.g., an increased antibody response and/or an increased T cell response) against a flavivirus such as a Zika virus. Any appropriate mammal can be administered a vaccine composition provided herein to increase an immune response against a flavivirus such as a Zika virus within that mammal. For example, humans, non-human primates (e.g., monkeys or apes), horses, dogs, cats, bovine species, pigs, sheep, mice, rats, goats, ducks, water buffaloes, and bats can be administered a vaccine composition provided herein to increase an immune response against a flavivirus such as a Zika virus. In some cases, a mammal identified as needing an increase in an immune response against a flavivirus such as a Zika virus can be administered a vaccine composition provided herein. For example, humans identified as having been in recent (e.g., within one to two weeks) contact with one or more humans having or suspected of having a flavivirus infection (e.g., a Zika virus infection) can be identified as needing an increase in an immune response against a flavivirus such as a Zika virus and can be administered a vaccine composition provided herein. In some cases, humans traveling or planning to travel to a location suspected of having prevalent flavivirus infections (e.g., Zika virus infections) or prior flavivirus infection (e.g., Zika virus infection) outbreaks can be identified as needing an increase in an immune response against a flavivirus such as a Zika virus and can be administered a vaccine composition provided herein. In some cases, a pregnant mammal (e.g., a pregnant human) can be administered a vaccine composition provided herein to increase an immune response against a flavivirus such as a Zika virus.

This document also provides methods for treating a mammal (e.g., a human) infected with a flavivirus such as a Zika virus. For example, a vaccine composition provided herein can be administered to a mammal (e.g., a human) having a Zika virus infection to reduce the severity of the Zika virus infection. Any appropriate mammal can be administered a vaccine composition provided herein to treat a flavivirus infection such as a Zika virus infection. For example, humans, non-human primates (e.g., monkeys or apes), horses, dogs, cats, bovine species, pigs, sheep, mice, rats, goats, ducks, water buffaloes, and bats can be administered a vaccine composition provided herein to treat a flavivirus infection such as a Zika virus infection. In some cases, a pregnant mammal (e.g., a pregnant human) can be administered a vaccine composition provided herein to treat a flavivirus infection such as a Zika virus infection. In some cases, a mammal that was identified as having a flavivirus infection such as a Zika virus infection can be administered a vaccine composition provided herein to treat that infection. Any appropriate method can be used to identify a mammal as having a flavivirus infection such as a Zika virus infection. For example, immunoassays can be used to identify a mammal (e.g., a human) as having antibodies specific for a flavivirus (e.g., a Zika virus). In some cases, the presence of flavivirus nucleic acid (e.g., Zika virus nucleic acid) within a sample obtained from a mammal can be detected, thereby indicating that the mammal has a flavivirus infection. Any appropriate sample can be obtained from a mammal to be tested and assessed as described herein. For example, biological samples such as fluid samples (e.g., blood (e.g., whole blood, plasma, and serum), urine, breast milk, saliva, amniotic fluid, cerebral spinal fluid, or semen) or tissue samples (e.g., placenta tissue samples) can be obtained from a mammal and assessed as described herein.

In some cases, a vaccine composition provided herein can be administered to a mammal (e.g., a human) having a flavivirus infection (e.g., a Zika virus infection) under conditions effective to reduce the duration and/or the severity of one or more symptoms or disease complications of the infection. Symptoms of flavivirus infection include, without limitation, fever, skin rash (e.g., maculopapular skin rash), muscle pain, joint pain, back pain, conjunctivitis, vomiting, headache, malaise, prostration, edema of the extremities, diarrhea, anorexia, dizziness, and more severe symptoms such as jaundice, renal failure, systemic shock, and death.

When administering a composition (e.g., a vaccine composition) provided herein to a mammal (e.g., a human), any appropriate route of administration can be used. For example, a composition (e.g., a vaccine composition) provided herein can be administered to a mammal (e.g., a human) intravenously (e.g., via an intravenous injection or infusion), subcutaneously (e.g., via a subcutaneous injection), intraperitoneally (e.g., via an intraperitoneal injection), orally, via inhalation, or intramuscularly (e.g., via intramuscular injection). In some cases, the route and/or mode of administration of a composition (e.g., a vaccine composition) provided herein can be adjusted for the mammal being treated.

Effective doses of a composition (e.g., a vaccine composition) provided herein can vary depending on the route of administration, the age and general health condition of the subject, excipient usage, the possibility of co-usage with other therapeutic treatments such as use of other agents, and the judgment of the treating physician. In some cases, an effective amount of a composition (e.g., a vaccine composition) provided herein can be an amount that increases an immune response against a flavivirus such as a Zika virus within the mammal (e.g., a human) without producing significant toxicity to the mammal. For example, an effective amount of a composition (e.g., a vaccine composition) provided herein can be from about 3 μg/dose to about 150 μg/dose (e.g. 3 μg/dose to 150 μg/dose, 5 μg/dose to 150 μg/dose, 10 μg/dose to 150 μg/dose, 15 μg/dose to 150 μg/dose, 20 μg/dose to 150 μg/dose, 25 μg/dose to 150 μg/dose, 30 μg/dose to 150 μg/dose, 3 μg/dose to 125 μg/dose, 3 μg/dose to 100 μg/dose, 3 μg/dose to 90 μg/dose, 3 μg/dose to 75 μg/dose, 10 μg/dose to 125 μg/dose, 15 μg/dose to 100 μg/dose, 15 μg/dose to 90 μg/dose, or 20 μg/dose to 75 μg/dose). In some cases, an effective amount of a composition (e.g., a vaccine composition) provided herein can be from about 3 μg of the total Zika virus polypeptide content of the composition to about 150 μg of the total Zika virus polypeptide content of the composition (e.g., 3 μg to 150 μg, 5 μg to 150 μg, 10 μg to 150 μg. 15 μg to 150 μg, 20 μg to 150 μg, 25 μg to 150 μg, 30 μg to 150 μg, 3 μg to 125 μg, 3 μg to 100 μg, 3 μg to 90 μg, 3 μg to 75 μg, 10 μg to 125 μg, 15 μg to 100 μg, 15 μg to 90 μg, or 20 μg to 75 μg of total Zika virus polypeptide content), with that total Zika virus polypeptide content being the sum of all polypeptides within the composition that comprise, consist essentially of, or consist of the amino acid sequence set forth in any of SEQ ID NOS:1-17.

This document also provides kits containing one or more (e.g., one, two, three, four, five, six, seven, eight, nine, ten, 11, 12, 13, 14, 15, 16, 17, 18, 19, 20, or more) polypeptides provided herein (e.g., one or more substantially pure polypeptides that comprise, consist essentially of, or consist of the amino acid sequence set forth in any of SEQ ID NOs:1-17). For example, a kit provided herein can include at least four (e.g., four, five, six, seven, or eight) of the polypeptides set forth in Table 1. In some cases, a kit provided herein can include each of the polypeptides set forth in Table 1. In some cases, a kit provided herein can include at least four (e.g., four, five, six, or seven) of the polypeptides set forth in Table 2. In some cases, a kit provided herein can include each of the polypeptides set forth in Table 2.

In some cases, a kit provided herein can be used to detect an immune response (e.g., a humoral antibody response or a cellular immune response) within a mammal (e.g., a human). For example, cells obtained from a mammal (e.g., a human) can be incubated with a kit provided herein that includes antigen presenting cells that present one or more of the polypeptides provided herein to detect the presence or absence of antigen specific T cells that have the ability to recognize one or more of the polypeptides included within the kit. In some cases, a kit provided herein can be used to detect antigen specific T cells post-vaccination of a mammal (e.g., a mammal administered a vaccine composition provided herein) to determine the efficacy of immunization. In some cases, a kit provided herein can be used to detect HLA class-II restricted T helper cells having the ability to recognize one or more of the polypeptides included within the kit. Any appropriate technique can be used to determine the presence or absence of cells (e.g., T cells such as HLA class-II restricted T helper cells) having the ability to recognize one or more of the polypeptides included within a kit provided herein. For example, flow cytometry, enzyme-linked immunospot (ELISPOT), cytokine secretion, direct cytotoxicity assays, and lymphoproliferation assays can be used to detect antigen specific T cells. In some cases, cytokine production and/or degranulation can be used as markers to determine the presence or absence of cells (e.g., T cells such as HLA class-II restricted T helper cells) having the ability to recognize one or more of the polypeptides included within a kit provided herein. Examples of cytokines that can be assessed include, without limitation, interferon gamma (IFN-gamma), tumor necrosis factor alpha (TNF-alpha), interleukin 2 (IL-2), interleukin 4 (IL-4), interleukin 5 (IL-5), interleukin 10 (IL-10), interferon alpha (IFN-alpha), transforming growth factor beta (TGF-beta), interleukin (IL-12), and interleukin 17 (IL-17). Examples of degranulation markers that can be assessed include, without limitation, intracellular expression of perforin, intracellular expression of granzyme B, or cell surface expression of CD107a. In some cases, a kit provided herein can include one or more of the polypeptides provided herein in the form of MHC-polypeptide tetramers that are labeled (e.g., covalently labeled) with a fluorochrome. In such cases, the labeled MHC-polypeptide tetramers of a kit provided herein can be used to bind to antigen-specific T cells within a sample, and the bound cells can be counted by flow cytometry As described herein, the methods and materials provided herein can be used to increase an immune response against a flavivirus within a mammal (e.g., a human), can be used to treat a mammal (e.g., a human) infected with a flavivirus, can be used to identify a mammal (e.g., a human) as having a flavivirus infection, and/or can be used to identify a mammal (e.g., a human) as having an immune response (e.g., a humoral antibody response or a cellular immune response) against a flavivirus. Examples of such flaviviruses include, without limitation, Zika virus, Dengue virus, West Nile virus, Yellow Fever virus, Spondweni virus, Japanese encephalitis virus, St. Louis encephalitis virus, Powassan virus, Tick borne encephalitis virus, Kyasanur Forest virus, Deer tick virus, Omsk hemorrhagic fever virus, Entebbe viruses, Modoc viruses, and Rio Bravo viruses. When the flavivirus is a Zika virus, the Zika virus can be any appropriate lineage, clade, or strain of Zika virus. Examples of such Zika viruses include, without limitation, East African Zika virus, West African Zika virus, Asian/Pacific Zika virus, and Asian/American Zika virus.

The invention will be further described in the following examples, which do not limit the scope of the invention described in the claims.

EXAMPLES

Example 1: Peptide-Based Vaccine Development Against Zika Virus

In this Example, immortalized human B cells expressing HLA-A*0201 and HLA-DRB1*0401 were infected with ZIKV, and polypeptides were isolated using acidic buffer to denature HLA molecules on the cell surface. Polypeptides were identified by two-dimensional (2D) liquid chromatography coupled with tandem mass spectrometry (LC-MS/MS). Polypeptides were subsequently analyzed using a suite of computational approaches to evaluate antigenic properties and binding to different HLA molecules. Synthetic polypeptides were used to screen IFN-γ T cell responses in immune cells from convalescent subjects.

Polypeptide Identification by Mass Spectrometry

Immortalized B cells homozygous for HLA-A*02:01 (A2 supertype) and HLA-DRB1*04:01 (DR4 supertype) were infected with ZIKV (PRVABC59, MOI=0.1) and cultured for 48 hours to allow for sufficient processing and presentation of viral proteins. Cells were treated with acidic citrate-phosphate buffer (pH=3.0) to denature HLA molecules and polypeptides were isolated from protein contaminants by centrifugal filtration. Polypeptides were further purified by fractionation using strong cation exchange (SCX) chromatography and analyzed by nanoscale liquid chromatographic tandem mass spectrometry (nLC-MS/MS). Deconvolution analysis with UniProt identified 90 polypeptides derived from viral proteins: 59 from non-structural (NS) protein 1 (NS1), 2 from NS2A, 7 from NS3, 4 from NS4B, 8 from NS5, 8 from capsid (C), and 2 from envelope (E). Redundant sequences or polypeptides with high degrees of sequence similarity (e.g., sequences nested within larger sequences) were excluded from further analysis, narrowing the list to 34 unique polypeptides for testing. Polypeptides were individually synthesized in large batches (5 mg) for functional testing.

Convalescent Subjects

Peripheral blood mononuclear cells (PBMCs) from 7 healthy human donors with prior documented ZIKV infections were used. Subjects are herein represented by their unique numerical study identifier: 591, 596, 602, 625, 626, 627, and 629. Subject 591 provided samples at two separate dates post-infection: ~21 days and ~138 days. These samples are subsequently denoted 591-1 and 591-3, respectively.

IFN-γ T cell ELISpot Recall Responses

Polypeptide Pool Stimulation

Viral polypeptides were randomly sorted into pools of 8-9 polypeptides with overlap between adjacent pools. PBMCs ($2\times10^5$ cells/well) were seeded in a 96-well, polyvinylidene fluoride (PVDF)-backed microtiter plate coated with anti-human IFN-γ antibody and treated with one of the following conditions: culture media (unstimulated), 20 μg pooled ZIKV polypeptides, ZIKV (MOI=1), or 20 μg pooled actin polypeptides as a negative control. Cells were incubated for 18 hours and recall immune responses were quantified using human IFN-γ ELISpot kits. Data was also grouped by subject to better visualize recall response profiles unique to each individual. Samples stimulated with ZIKV polypeptides or live virus were tested in triplicate: unstimulated samples and negative controls were tested in quadruplicate. Responses were highly variable between polypeptide pools and individual subjects, and pools stimulating a positive IFN-γ ELISpot response in at least one subject were subsequently analyzed at the individual polypeptide level against the responding subject(s).

Individual Polypeptide Stimulation

PBMCs ($2\times10^5$ cells/well) were seeded in a 96-well, PVDF-backed microtiter plate coated with anti-human IFN-γ antibody and treated with one of the following conditions: culture media (unstimulated), 10 μg individual ZIKV peptides, ZIKV (MOI=1), or 20 μg pooled actin polypeptides as a negative control. Cells were incubated for 18 hours and recall immune responses were quantified using human IFN-γ ELISpot kits. Samples stimulated with ZIKV polypeptides or live virus were tested in triplicate: unstimulated samples and negative controls were tested in quadruplicate. Nine polypeptides that stimulated a positive recall immune response in 4 of 7 subjects (Table 1) were selected as leading ZIKV derived polypeptides for detailed informatics analyses. Eight polypeptides that stimulated a limited recall response (1 of 7 subjects: Table 2) were selected as comparators.

Modeling of Polypeptide Structure and Properties

The structures of all ZIKV derived polypeptides set forth in SEQ ID NOs:1-9 and comparator polypeptides were modeled using PEP-FOLD 3.5, an online server that predicts polypeptide structure based on the properties of each amino acid in the sequence. Properties of the individual polypeptides in both groups were determined in silico using the Protparam tool hosted on the Expasy server. Polypeptides set forth in SEQ ID NOs:1-9 were largely predicted to have ordered structures that adopted some degree of helical conformation when modeled under physiological conditions. In contrast, the majority of the comparator polypeptides (5 of 8) adopted largely disordered structures exhibiting high degrees of coiled and extended structural features under the same modeling parameters. The ZIKV derived polypeptides set forth in SEQ ID NOs:1-9 were predicted to have a longer theoretical half-life than the comparator group (16.21 hours vs. 8.99 hours), which correlated with the average instability index for the two groups (24.72 vs. 43.75). A larger instability index (>40) is indicative of an unstable polypeptide structure. The ZIKV derived polypeptides set forth in SEQ ID NOs:1-9 also were predicted to have a larger average aliphatic index than the comparator group (125.41 vs. 103.67), which is a positive metric for thermostability. The grand average of hydropathy (GRAVY) index differed between the ZIKV derived polypeptides set forth in SEQ ID NOs:1-9 and comparator groups (0.27 vs. −0.24), indicating the comparator polypeptides were slightly more hydrophilic. Polypeptide stability can be used in the design of polypeptide-based vaccines and therapeutics, and collectively, these modeling data suggest that the ZIKV derived polypeptides set forth in SEQ ID NOs:1-9 are stable for formulation and use as components of a ZIKV vaccine.

Optimized IFN-γ ELISpot Recall Response

The analysis of IFN-γ ELISpot recall responses was revised to focus only on clusters of ZIKV derived polypeptides set forth in SEQ ID NOs:1-9 and comparator polypeptides. A dense cluster of polypeptides eliciting recall responses was observed in the ZIKV derived polypeptides set forth in SEQ ID NOs:1-9 among convalescent subjects as expected, while the comparator cluster exhibited a very narrow response profile across subjects. Subjects 602 and 625 were the strongest responders in the comparator group, with subject 625 responding to 4 of the 8 epitopes (FIG. 1). Three subjects (626, 596, and 629) did not respond to any of the polypeptides in the comparator group. In contrast, all subjects exhibited recall responses to at least three polypeptides in the ZIKV derived polypeptides set forth in SEQ ID NOs:1-9, illustrating the breadth of coverage provided by the ZIKV derived polypeptides set forth in SEQ ID NOs:1-9.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising at least four polypeptides, wherein each of said at least four polypeptides is a polypeptide consisting of the amino acid sequence set forth in any one of SEQ ID NOs: 1-17, and wherein at least one of said at least four polypeptides is covalently conjugated to a stabilizer selected from the group consisting of sucrose, lactose, a monosodium salt of glutamic acid, human serum albumin, and gelatin.

2. The composition of claim 1, wherein said each of said at least four polypeptides is a polypeptide consisting of the amino acid sequence set forth in any one of SEQ ID NOs:1-9.

3. The composition of claim 1, wherein said composition comprises a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:3, a polypeptide consisting of the amino acid sequence set forth in SEQ ID NO:4, a polypeptide consisting of the amino acid sequence set forth in SEQ ID NO:5, a polypeptide consisting of the amino acid sequence set forth in SEQ ID NO:6, a polypeptide consisting of the amino acid sequence set forth in SEQ ID NO:7, a polypeptide consisting of the amino acid sequence set forth in SEQ ID NO:8, and a polypeptide consisting of the amino acid sequence set forth in SEQ ID NO:9.

4. The composition of claim 3, wherein said composition further comprises an adjuvant selected from the group consisting of a CpG oligonucleotide motif, aluminum sulfate, aluminum hydroxide, aluminum phosphate, aluminum potassium sulfate, monophosphoryl lipid A, aluminumphosphylate, an oil-in-water emulsion comprising squalene, polysorbate 80, and sorbitan trioleate, an oil-in-water emulsion comprising squalene, polysorbate 80, sorbitan trioleate, and alpha-tocopherol, and a combination of aluminum hydroxide and monophosphoryl lipid A.

5. A composition comprising at least four polypeptides, wherein each of said at least four polypeptides is a polypeptide consisting of an amino acid sequence selected from the group consisting of SEQ ID NOs:1-17, and wherein at least one of said at least four polypeptides is embedded on the surface of a nanoparticle.

6. The composition of claim 5, wherein said each of said at least four polypeptides is a polypeptide consisting of the amino acid sequence set forth in any one of SEQ ID NOs:1-9.

7. The composition of claim 5, wherein said composition comprises a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:3, a polypeptide consisting of the amino acid sequence set forth in SEQ ID NO:4, a polypeptide consisting of the amino acid sequence set forth in SEQ ID NO:5, a polypeptide consisting of the amino acid sequence set forth in SEQ ID NO:6, a polypeptide consisting of the amino acid sequence set forth in SEQ ID NO:7, a polypeptide consisting of the amino acid sequence set forth in SEQ ID NO:8, and a polypeptide consisting of the amino acid sequence set forth in SEQ ID NO:9.

8. The composition of claim 5, wherein said composition further comprises an adjuvant selected from the group consisting of a CpG oligonucleotide motif, aluminum sulfate, aluminum hydroxide, aluminum phosphate, aluminum potassium sulfate, monophosphoryl lipid A, aluminumphosphylate, an oil-in-water emulsion comprising squalene, polysorbate 80, and sorbitan trioleate, an oil-in-water emulsion comprising squalene, polysorbate 80, sorbitan trioleate, and alpha-tocopherol, and a combination of aluminum hydroxide and monophosphoryl lipid A.

9. A method for increasing an immune response against a flavivirus in a mammal, wherein said method comprises administering to said mammal a composition comprising at least four polypeptides, wherein each of said at least four polypeptides is a polypeptide consisting of the amino acid sequence set forth in any one of SEQ ID NOs:1-17, and wherein at least one of said at least four polypeptides is covalently conjugated to a stabilizer selected from the group consisting of sucrose, lactose, a monosodium salt of glutamic acid, human serum albumin, and gelatin.

10. The method of claim 9, wherein said mammal is a human.

11. The method of claim 9, wherein said flavivirus is a Zika virus.

12. The method of claim 9, wherein said composition further comprises an adjuvant.

13. The method of claim 12, wherein said adjuvant is selected from the group consisting of a CpG oligonucleotide motif, aluminum sulfate, aluminum hydroxide, aluminum phosphate, aluminum potassium sulfate, monophosphoryl lipid A, aluminumphosphylate, an oil-in-water emulsion comprising squalene, polysorbate 80, and sorbitan trioleate, an oil-in-water emulsion comprising squalene, polysorbate 80, sorbitan trioleate, and alpha-tocopherol, and a combination of aluminum hydroxide and monophosphoryl lipid A.

14. The method of claim 9, wherein said each of said at least four polypeptides is a polypeptide consisting of the amino acid sequence set forth in any one of SEQ ID NOs:1-9.

15. The method of claim 9, wherein said composition comprises a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:3, a polypeptide consisting of the amino acid sequence set forth in SEQ ID NO:4, a polypeptide consisting of the amino acid sequence set forth in SEQ ID NO:5, a polypeptide consisting of the amino acid sequence set forth in SEQ ID NO:6, a polypeptide consisting of the amino acid sequence set forth in SEQ ID NO:7, a polypeptide consisting of the amino acid sequence set forth in SEQ ID NO:8, and a polypeptide consisting of the amino acid sequence set forth in SEQ ID NO:9.

16. A method for increasing an immune response against a flavivirus in a mammal, wherein said method comprises administering to said mammal a composition comprising at least four polypeptides, wherein each of said at least four polypeptides is a polypeptide consisting of an amino acid sequence selected from the group consisting of SEQ ID NOs:1-17, and wherein at least one of said at least four polypeptides is embedded on the surface of a nanoparticle.

17. The method of claim 16, wherein said mammal is a human.

18. The method of claim 16, wherein said flavivirus is a Zika virus.

19. The method of claim 16, wherein said composition further comprises an adjuvant.

20. The method of claim 19, wherein said adjuvant is selected from the group consisting of a CpG oligonucleotide motif, aluminum sulfate, aluminum hydroxide, aluminum phosphate, aluminum potassium sulfate, monophosphoryl lipid A, aluminumphosphylate, an oil-in-water emulsion comprising squalene, polysorbate 80, and sorbitan trioleate, an oil-in-water emulsion comprising squalene, polysorbate 80, sorbitan trioleate, and alpha-tocopherol, and a combination of aluminum hydroxide and monophosphoryl lipid A.

21. The method of claim 20, wherein said each of said at least four polypeptides is a polypeptide consisting of the amino acid sequence set forth in any one of SEQ ID NOs:1-9.

22. The method of claim 16, wherein said composition comprises a polypeptide consisting of the amino acid sequence set forth in SEQ ID NO:1, a polypeptide consisting of the amino acid sequence set forth in SEQ ID NO:2, a polypeptide consisting of the amino acid sequence set forth in SEQ ID NO:3, a polypeptide consisting of the amino acid sequence set forth in SEQ ID NO:4, a polypeptide consisting of the amino acid sequence set forth in SEQ ID NO:5, a polypeptide consisting of the amino acid sequence set forth in SEQ ID NO:6, a polypeptide consisting of the amino acid sequence set forth in SEQ ID NO:7, a polypeptide consisting of the amino acid sequence set forth in SEQ ID NO:8, and a polypeptide consisting of the amino acid sequence set forth in SEQ ID NO:9.

* * * * *

SEQUENCE LISTING

```
<160> NUMBER OF SEQ ID NOS: 61

<210> SEQ ID NO 1
<211> LENGTH: 10
<212> TYPE: PRT
<213> ORGANISM: Zika virus

<400> SEQUENCE: 1

Tyr Leu Gln Asp Gly Leu Ile Ala Ser Leu
1               5                   10


<210> SEQ ID NO 2
<211> LENGTH: 23
<212> TYPE: PRT
<213> ORGANISM: Zika virus

<400> SEQUENCE: 2

Thr Val Val Val Gly Ser Val Lys Asn Pro Met Trp Arg Gly Pro Gln
1               5                   10                  15

Arg Leu Pro Val Pro Val Asn
            20


<210> SEQ ID NO 3
<211> LENGTH: 12
<212> TYPE: PRT
<213> ORGANISM: Zika virus

<400> SEQUENCE: 3

Phe Leu Arg Phe Thr Ala Ile Lys Pro Ser Leu Gly
1               5                   10


<210> SEQ ID NO 4
<211> LENGTH: 9
<212> TYPE: PRT
<213> ORGANISM: Zika virus

<400> SEQUENCE: 4

Gln Val Ala Ser Ala Gly Ile Thr Tyr
1               5


<210> SEQ ID NO 5
<211> LENGTH: 9
<212> TYPE: PRT
<213> ORGANISM: Zika virus

<400> SEQUENCE: 5

Ser Leu Ile Asn Gly Val Val Arg Leu
1               5
```

<210> SEQ ID NO 6
<211> LENGTH: 17
<212> TYPE: PRT
<213> ORGANISM: Zika virus

<400> SEQUENCE: 6

Gly Gly Leu Lys Arg Leu Pro Ala Gly Leu Leu Leu Gly His Gly Pro
1 5 10 15

Ile

<210> SEQ ID NO 7
<211> LENGTH: 8
<212> TYPE: PRT
<213> ORGANISM: Zika virus

<400> SEQUENCE: 7

Val Val Asp Gly Asp Thr Leu Lys
1 5

<210> SEQ ID NO 8
<211> LENGTH: 17
<212> TYPE: PRT
<213> ORGANISM: Zika virus

<400> SEQUENCE: 8

Asp Gly Ile Glu Glu Ser Asp Leu Ile Ile Pro Lys Ser Leu Ala Gly
1 5 10 15

Pro

<210> SEQ ID NO 9
<211> LENGTH: 9
<212> TYPE: PRT
<213> ORGANISM: Zika virus

<400> SEQUENCE: 9

Arg Ile Ile Gly Asp Glu Glu Lys Tyr
1 5

<210> SEQ ID NO 10
<211> LENGTH: 10
<212> TYPE: PRT
<213> ORGANISM: Zika virus

<400> SEQUENCE: 10

Gly Arg Gly Pro Gln Arg Leu Pro Val Pro
1 5 10

<210> SEQ ID NO 11
<211> LENGTH: 9
<212> TYPE: PRT
<213> ORGANISM: Zika virus

<400> SEQUENCE: 11

Ala Leu Ala Leu Ala Ile Ile Lys Tyr
1 5

<210> SEQ ID NO 12
<211> LENGTH: 13
<212> TYPE: PRT
<213> ORGANISM: Zika virus

<400> SEQUENCE: 12

```
Arg Gln Asp Gln Arg Gly Ser Gly Gln Val Val Thr Tyr
1               5                   10


<210> SEQ ID NO 13
<211> LENGTH: 12
<212> TYPE: PRT
<213> ORGANISM: Zika virus

<400> SEQUENCE: 13

Thr Val Thr Arg Asn Ala Gly Leu Val Lys Arg Arg
1               5                   10


<210> SEQ ID NO 14
<211> LENGTH: 9
<212> TYPE: PRT
<213> ORGANISM: Zika virus

<400> SEQUENCE: 14

Tyr Leu Ile Pro Gly Leu Gln Ala Ala
1               5


<210> SEQ ID NO 15
<211> LENGTH: 24
<212> TYPE: PRT
<213> ORGANISM: Zika virus

<400> SEQUENCE: 15

Leu Thr Val Val Val Gly Ser Val Lys Asn Pro Met Gly Arg Gly Pro
1               5                   10                  15

Gln Arg Leu Pro Val Pro Val Asn
            20


<210> SEQ ID NO 16
<211> LENGTH: 22
<212> TYPE: PRT
<213> ORGANISM: Zika virus

<400> SEQUENCE: 16

Ile Ile Pro Lys Ser Leu Ala Gly Pro Leu Ser His His Asn Thr Arg
1               5                   10                  15

Glu Gly Tyr Arg Thr Gln
            20


<210> SEQ ID NO 17
<211> LENGTH: 11
<212> TYPE: PRT
<213> ORGANISM: Zika virus

<400> SEQUENCE: 17

Arg Gly Pro Gln Arg Leu Pro Val Pro Val Asn
1               5                   10


<210> SEQ ID NO 18
<211> LENGTH: 20
<212> TYPE: PRT
<213> ORGANISM: Zika virus

<400> SEQUENCE: 18

Leu Leu Asp Asn Ile Tyr Leu Gln Asp Gly Leu Ile Ala Ser Leu Tyr
1               5                   10                  15

Arg Pro Glu Ala
            20
```

<210> SEQ ID NO 19
<211> LENGTH: 18
<212> TYPE: PRT
<213> ORGANISM: Zika virus

<400> SEQUENCE: 19

Leu Asp Asn Ile Tyr Leu Gln Asp Gly Leu Ile Ala Ser Leu Tyr Arg
1               5                   10                  15

Pro Glu

<210> SEQ ID NO 20
<211> LENGTH: 16
<212> TYPE: PRT
<213> ORGANISM: Zika virus

<400> SEQUENCE: 20

Asp Asn Ile Tyr Leu Gln Asp Gly Leu Ile Ala Ser Leu Tyr Arg Pro
1               5                   10                  15

<210> SEQ ID NO 21
<211> LENGTH: 14
<212> TYPE: PRT
<213> ORGANISM: Zika virus

<400> SEQUENCE: 21

Asn Ile Tyr Leu Gln Asp Gly Leu Ile Ala Ser Leu Tyr Arg
1               5                   10

<210> SEQ ID NO 22
<211> LENGTH: 12
<212> TYPE: PRT
<213> ORGANISM: Zika virus

<400> SEQUENCE: 22

Ile Tyr Leu Gln Asp Gly Leu Ile Ala Ser Leu Tyr
1               5                   10

<210> SEQ ID NO 23
<211> LENGTH: 64
<212> TYPE: PRT
<213> ORGANISM: Zika virus

<400> SEQUENCE: 23

Asn Gly Val Gln Leu Thr Val Val Val Gly Ser Val Lys Asn Pro Met
1               5                   10                  15

Gly Arg Gly Pro Gln Arg Leu Pro Val Pro Val Asn Glu Leu Pro His
            20                  25                  30

Gly Gly Val Gln Leu Thr Val Val Val Gly Ser Val Lys Asn Pro Met
        35                  40                  45

Gly Arg Gly Pro Gln Arg Leu Pro Val Pro Val Asn Glu Leu Pro His
    50                  55                  60

<210> SEQ ID NO 24
<211> LENGTH: 29
<212> TYPE: PRT
<213> ORGANISM: Zika virus

<400> SEQUENCE: 24

Val Gln Leu Thr Val Val Val Gly Ser Val Lys Asn Pro Met Gly Arg
1               5                   10                  15

Gly Pro Gln Arg Leu Pro Val Pro Val Asn Glu Leu Pro
            20                  25

<210> SEQ ID NO 25
<211> LENGTH: 27
<212> TYPE: PRT
<213> ORGANISM: Zika virus

<400> SEQUENCE: 25

Gln Leu Thr Val Val Val Gly Ser Val Lys Asn Pro Met Gly Arg Gly
1 5 10 15

Pro Gln Arg Leu Pro Val Pro Val Asn Glu Leu
20 25

<210> SEQ ID NO 26
<211> LENGTH: 25
<212> TYPE: PRT
<213> ORGANISM: Zika virus

<400> SEQUENCE: 26

Leu Thr Val Val Val Gly Ser Val Lys Asn Pro Met Gly Arg Gly Pro
1 5 10 15

Gln Arg Leu Pro Val Pro Val Asn Glu
20 25

<210> SEQ ID NO 27
<211> LENGTH: 22
<212> TYPE: PRT
<213> ORGANISM: Zika virus

<400> SEQUENCE: 27

Leu Ala Ile Leu Ala Phe Leu Arg Phe Thr Ala Ile Lys Pro Ser Leu
1 5 10 15

Gly Leu Ile Asn Arg Trp
20

<210> SEQ ID NO 28
<211> LENGTH: 20
<212> TYPE: PRT
<213> ORGANISM: Zika virus

<400> SEQUENCE: 28

Ala Ile Leu Ala Phe Leu Arg Phe Thr Ala Ile Lys Pro Ser Leu Gly
1 5 10 15

Leu Ile Asn Arg
20

<210> SEQ ID NO 29
<211> LENGTH: 18
<212> TYPE: PRT
<213> ORGANISM: Zika virus

<400> SEQUENCE: 29

Ile Leu Ala Phe Leu Arg Phe Thr Ala Ile Lys Pro Ser Leu Gly Leu
1 5 10 15

Ile Asn

<210> SEQ ID NO 30
<211> LENGTH: 16
<212> TYPE: PRT
<213> ORGANISM: Zika virus

<400> SEQUENCE: 30

Leu Ala Phe Leu Arg Phe Thr Ala Ile Lys Pro Ser Leu Gly Leu Ile
1 5 10 15

<210> SEQ ID NO 31
<211> LENGTH: 14
<212> TYPE: PRT
<213> ORGANISM: Zika virus

<400> SEQUENCE: 31

Ala Phe Leu Arg Phe Thr Ala Ile Lys Pro Ser Leu Gly Leu
1 5 10

<210> SEQ ID NO 32
<211> LENGTH: 19
<212> TYPE: PRT
<213> ORGANISM: Zika virus

<400> SEQUENCE: 32

Val Trp Leu Ala Tyr Gln Val Ala Ser Ala Gly Ile Thr Tyr Thr Asp
1 5 10 15

Arg Arg Trp

<210> SEQ ID NO 33
<211> LENGTH: 17
<212> TYPE: PRT
<213> ORGANISM: Zika virus

<400> SEQUENCE: 33

Trp Leu Ala Tyr Gln Val Ala Ser Ala Gly Ile Thr Tyr Thr Asp Arg
1 5 10 15

Arg

<210> SEQ ID NO 34
<211> LENGTH: 15
<212> TYPE: PRT
<213> ORGANISM: Zika virus

<400> SEQUENCE: 34

Leu Ala Tyr Gln Val Ala Ser Ala Gly Ile Thr Tyr Thr Asp Arg
1 5 10 15

<210> SEQ ID NO 35
<211> LENGTH: 13
<212> TYPE: PRT
<213> ORGANISM: Zika virus

<400> SEQUENCE: 35

Ala Tyr Gln Val Ala Ser Ala Gly Ile Thr Tyr Thr Asp
1 5 10

<210> SEQ ID NO 36
<211> LENGTH: 11
<212> TYPE: PRT
<213> ORGANISM: Zika virus

<400> SEQUENCE: 36

Tyr Gln Val Ala Ser Ala Gly Ile Thr Tyr Thr
1 5 10

<210> SEQ ID NO 37
<211> LENGTH: 19
<212> TYPE: PRT
<213> ORGANISM: Zika virus

<400> SEQUENCE: 37

```
Gln Gly Ser Ala Ser Ser Leu Ile Asn Gly Val Val Arg Leu Leu Ser
1               5                   10                  15

Lys Pro Trp


<210> SEQ ID NO 38
<211> LENGTH: 17
<212> TYPE: PRT
<213> ORGANISM: Zika virus

<400> SEQUENCE: 38

Gly Ser Ala Ser Ser Leu Ile Asn Gly Val Val Arg Leu Leu Ser Lys
1               5                   10                  15

Pro


<210> SEQ ID NO 39
<211> LENGTH: 15
<212> TYPE: PRT
<213> ORGANISM: Zika virus

<400> SEQUENCE: 39

Ser Ala Ser Ser Leu Ile Asn Gly Val Val Arg Leu Leu Ser Lys
1               5                   10                  15


<210> SEQ ID NO 40
<211> LENGTH: 13
<212> TYPE: PRT
<213> ORGANISM: Zika virus

<400> SEQUENCE: 40

Ala Ser Ser Leu Ile Asn Gly Val Val Arg Leu Leu Ser
1               5                   10


<210> SEQ ID NO 41
<211> LENGTH: 11
<212> TYPE: PRT
<213> ORGANISM: Zika virus

<400> SEQUENCE: 41

Ser Ser Leu Ile Asn Gly Val Val Arg Leu Leu
1               5                   10


<210> SEQ ID NO 42
<211> LENGTH: 27
<212> TYPE: PRT
<213> ORGANISM: Zika virus

<400> SEQUENCE: 42

Arg Val Ser Pro Phe Gly Gly Leu Lys Arg Leu Pro Ala Gly Leu Leu
1               5                   10                  15

Leu Gly His Gly Pro Ile Arg Met Val Leu Ala
            20                  25


<210> SEQ ID NO 43
<211> LENGTH: 25
<212> TYPE: PRT
<213> ORGANISM: Zika virus

<400> SEQUENCE: 43

Val Ser Pro Phe Gly Gly Leu Lys Arg Leu Pro Ala Gly Leu Leu Leu
1               5                   10                  15

Gly His Gly Pro Ile Arg Met Val Leu
            20                  25
```

<210> SEQ ID NO 44
<211> LENGTH: 23
<212> TYPE: PRT
<213> ORGANISM: Zika virus

<400> SEQUENCE: 44

```
Ser Pro Phe Gly Gly Leu Lys Arg Leu Pro Ala Gly Leu Leu Leu Gly
1               5                   10                  15

His Gly Pro Ile Arg Met Val
            20
```

<210> SEQ ID NO 45
<211> LENGTH: 21
<212> TYPE: PRT
<213> ORGANISM: Zika virus

<400> SEQUENCE: 45

```
Pro Phe Gly Gly Leu Lys Arg Leu Pro Ala Gly Leu Leu Leu Gly His
1               5                   10                  15

Gly Pro Ile Arg Met
            20
```

<210> SEQ ID NO 46
<211> LENGTH: 19
<212> TYPE: PRT
<213> ORGANISM: Zika virus

<400> SEQUENCE: 46

```
Phe Gly Gly Leu Lys Arg Leu Pro Ala Gly Leu Leu Leu Gly His Gly
1               5                   10                  15

Pro Ile Arg
```

<210> SEQ ID NO 47
<211> LENGTH: 18
<212> TYPE: PRT
<213> ORGANISM: Zika virus

<400> SEQUENCE: 47

```
Thr Asn Asn Ser Phe Val Val Asp Gly Asp Thr Leu Lys Glu Cys Pro
1               5                   10                  15

Leu Lys
```

<210> SEQ ID NO 48
<211> LENGTH: 16
<212> TYPE: PRT
<213> ORGANISM: Zika virus

<400> SEQUENCE: 48

```
Asn Asn Ser Phe Val Val Asp Gly Asp Thr Leu Lys Glu Cys Pro Leu
1               5                   10                  15
```

<210> SEQ ID NO 49
<211> LENGTH: 14
<212> TYPE: PRT
<213> ORGANISM: Zika virus

<400> SEQUENCE: 49

```
Asn Ser Phe Val Val Asp Gly Asp Thr Leu Lys Glu Cys Pro
1               5                   10
```

<210> SEQ ID NO 50
<211> LENGTH: 12

<212> TYPE: PRT
<213> ORGANISM: Zika virus

<400> SEQUENCE: 50

Ser Phe Val Val Asp Gly Asp Thr Leu Lys Glu Cys
1 5 10

<210> SEQ ID NO 51
<211> LENGTH: 10
<212> TYPE: PRT
<213> ORGANISM: Zika virus

<400> SEQUENCE: 51

Phe Val Val Asp Gly Asp Thr Leu Lys Glu
1 5 10

<210> SEQ ID NO 52
<211> LENGTH: 27
<212> TYPE: PRT
<213> ORGANISM: Zika virus

<400> SEQUENCE: 52

His Thr Leu Trp Thr Asp Gly Ile Glu Glu Ser Asp Leu Ile Ile Pro
1 5 10 15

Lys Ser Leu Ala Gly Pro Leu Ser His His Asn
20 25

<210> SEQ ID NO 53
<211> LENGTH: 25
<212> TYPE: PRT
<213> ORGANISM: Zika virus

<400> SEQUENCE: 53

Thr Leu Trp Thr Asp Gly Ile Glu Glu Ser Asp Leu Ile Ile Pro Lys
1 5 10 15

Ser Leu Ala Gly Pro Leu Ser His His
20 25

<210> SEQ ID NO 54
<211> LENGTH: 23
<212> TYPE: PRT
<213> ORGANISM: Zika virus

<400> SEQUENCE: 54

Leu Trp Thr Asp Gly Ile Glu Glu Ser Asp Leu Ile Ile Pro Lys Ser
1 5 10 15

Leu Ala Gly Pro Leu Ser His
20

<210> SEQ ID NO 55
<211> LENGTH: 21
<212> TYPE: PRT
<213> ORGANISM: Zika virus

<400> SEQUENCE: 55

Trp Thr Asp Gly Ile Glu Glu Ser Asp Leu Ile Ile Pro Lys Ser Leu
1 5 10 15

Ala Gly Pro Leu Ser
20

<210> SEQ ID NO 56
<211> LENGTH: 19
<212> TYPE: PRT

-continued

<213> ORGANISM: Zika virus

<400> SEQUENCE: 56

Thr Asp Gly Ile Glu Glu Ser Asp Leu Ile Ile Pro Lys Ser Leu Ala
1 5 10 15

Gly Pro Leu

<210> SEQ ID NO 57
<211> LENGTH: 19
<212> TYPE: PRT
<213> ORGANISM: Zika virus

<400> SEQUENCE: 57

Val Asn Met Val Arg Arg Ile Ile Gly Asp Glu Glu Lys Tyr Met Asp
1 5 10 15

Tyr Leu Ser

<210> SEQ ID NO 58
<211> LENGTH: 17
<212> TYPE: PRT
<213> ORGANISM: Zika virus

<400> SEQUENCE: 58

Asn Met Val Arg Arg Ile Ile Gly Asp Glu Glu Lys Tyr Met Asp Tyr
1 5 10 15

Leu

<210> SEQ ID NO 59
<211> LENGTH: 15
<212> TYPE: PRT
<213> ORGANISM: Zika virus

<400> SEQUENCE: 59

Met Val Arg Arg Ile Ile Gly Asp Glu Glu Lys Tyr Met Asp Tyr
1 5 10 15

<210> SEQ ID NO 60
<211> LENGTH: 13
<212> TYPE: PRT
<213> ORGANISM: Zika virus

<400> SEQUENCE: 60

Val Arg Arg Ile Ile Gly Asp Glu Glu Lys Tyr Met Asp
1 5 10

<210> SEQ ID NO 61
<211> LENGTH: 11
<212> TYPE: PRT
<213> ORGANISM: Zika virus

<400> SEQUENCE: 61

Arg Arg Ile Ile Gly Asp Glu Glu Lys Tyr Met
1 5 10